US00PP18939P2

(12) United States Plant Patent
Smith

(10) Patent No.: US PP18,939 P2
(45) Date of Patent: Jun. 17, 2008

(54) *HIBISCUS* PLANT NAMED 'PEPPERMINT SCHNAPPS'

(50) Latin Name: *Hibiscus hybrid*
Varietal Denomination: Peppermint Schnapps

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,533

(22) Filed: Dec. 18, 2006

(51) Int. Cl.
*A01H 5/00* (2006.01)

(52) U.S. Cl. ..... Plt./257
(58) Field of Classification Search ..... Plt./257
See application file for complete search history.

(56) References Cited

PUBLICATIONS

UPOV ROM GTITM Computer Database, GIT Jouve Retrieval Software 2007/02 Citation for 'Peppermint Schnapps'.*

* cited by examiner

*Primary Examiner*—Wendy C. Haas
(74) *Attorney, Agent, or Firm*—C. A. Whealy

(57) ABSTRACT

A new and distinct cultivar of Hardy *Hibiscus* plant named 'Peppermint Schnapps', characterized by its upright and outwardly spreading plant habit; green-colored leaves that are palmately lobed; early flowering habit; and large single pink-colored flowers with red purple-colored centers and venation.

1 Drawing Sheet

Botanical designation: *Hibiscus* hybrid.
Cultivar denomination: 'Peppermint Schnapps'.

BACKGROUND OF THE INVENTION

The present invention relates to a new and distinct cultivar of *Hibiscus,* botanically known as *Hibiscus* hybrid, commercially referred to as Hardy *Hibiscus* and hereinafter referred to by the name 'Peppermint Schnapps'.

The new *Hibiscus* is a product of a planned breeding program conducted by the Inventor in Alva, Fla. The objective of the breeding program is to create new freely-branching Hardy Hibiscus cultivars with a compact plant habit and desirable flower color.

The new Hardy *Hibiscus* originated from a cross-pollination made by the Inventor in Alva, Fla. during the summer of 2000, of an unnamed sport of the *Hibiscus* hybrid cultivar Disco Belle Pink, not patented, as the female, or seed, parent with an unnamed selection of *Hibiscus coccineus,* not patented, as the male, or pollen, parent. The cultivar Peppermint Schnapps was discovered and selected by the Inventor as a flowering plant within the progeny of the stated cross-pollination in a controlled environment in Alva, Fla. on May 29, 2001.

Asexual reproduction of the new Hardy *Hibiscus* by vegetative terminal cuttings in a controlled environment in Alva., Fla. since June, 2001, has shown that the unique features of this new Hardy *Hibiscus* are stable and reproduced true to type in successive generations.

SUMMARY OF THE INVENTION

The cultivar Peppermint Schnapps has not been observed under all possible environmental conditions. The phenotype may vary somewhat with variations in environmental and cultural practices such as temperature and light intensity without, however, any variance in genotype.

The following traits have been repeatedly observed and are determined to be the unique characteristics of 'Peppermint Schapps'. These characteristics in combination distinguish 'Peppermint Schnapps' as a new and distinct cultivar of Hardy *Hibiscus:*

1. Upright and outwardly spreading plant habit.
2. Green-colored leaves that are palmately lobed.
3. Early flowering habit.
4. Large single pink-colored flowers with red purple-colored centers and venation.

Plants of the new Hardy *Hibiscus* can be compared to plants of the female parent. In side-by-side comparisons conducted in Alva, Fla., plants of the new Hardy *Hibiscus* differed from plants of the female parent in the following characteristics:

1. Plants of the new Hardy *Hibiscus* were taller than plants of the female parent.
2. Plants of the new Hardy *Hibiscus* and the female parent differed in leaf form and color.
3. Plants of the new Hardy *Hibiscus* flowered later than plants of the female parent.
4. Flowers of plants of the new Hardy *Hibiscus* and the female parent differed in flower color.

Plants of the new Hardy *Hibiscus* can be compared to plants of the male parent selection. In side-by-side comparisons conducted in Alva, Fla., plants of the new Hardy *Hibiscus* differed from plants of the male parent selection in the following characteristics:

1. Plants of the new Hardy *Hibiscus* were more freely branching and denser than plants of the male parent selection.
2. Plants of the new Hardy *Hibiscus* and the male parent selection differed in leaf form and color.
3. Plants of the new Hardy *Hibiscus* flowered earlier than plants of the male parent selection.

4. Plants of the new Hardy *Hibiscus* had larger flowers than plants of the male parent selection.
5. Plants of the new Hardy *Hibiscus* and the male parent selection differed in flower color.

Plants of the new Hardy *Hibiscus* can be compared to plants of the *Hibiscus* hybrid cultivar Fantasia, disclosed in U.S. Plant Pat. No. 11,853. In side-by-side comparison conducted in Alva, Fla., plants of the new Hardy *Hibiscus* differed from plants of the cultivar Fantasia in the following characteristics:

1. Plants of the new Hardy *Hibiscus* were taller than plants of the cultivar Fantasia.
2. Plants of the new Hardy *Hibiscus* were more freely branching and denser than plants of the cultivar Fantasia.
3. Plants of the new Hardy *Hibiscus* and the cultivar Fantasia differed in leaf color.
4. Plants of the new Hardy *Hibiscus* flowered earlier than plants of the cultivar Fantasia.
5. Plants of the new Hardy *Hibiscus* and the cultivar Fantasia differed in flower color.

BRIEF DESCRIPTION OF THE PHOTOGRAPHS

The accompanying colored photographs illustrate the overall appearance of the new Hardy *Hibiscus,* showing the colors as true as it is reasonably possible to obtain in colored reproductions of this type. Colors in the photographs may differ slightly from the color values cited in the detailed botanical description which accurately describe the colors of the new Hardy *Hibiscus.*

The photograph at the bottom of the sheet comprises a side perspective view of a typical flowering plant of 'Peppermint Schnapps' grown in a container.

The photograph at the top of the sheet comprises a close-up view of a typical flower of 'Peppermint Schnapps'.

DETAILED BOTANICAL DESCRIPTION

The aforementioned photographs and following observations, measurements and values describe plants grown during the summer in Alva, Fla. in 1.5-gallon containers in a polypropylene-covered shadehouse and under conditions which closely approximate commercial Hardy *Hibiscus* production. During the production of the plants, day temperatures ranged from about 29° C. to about 35° C. and night temperatures ranged from about 21° C. to about 24° C. Plants were pinched one time and were about two months old when the photographs and the description were taken. In the description, color references are made to The Royal Horticultural Society Colour Chart, 1995 Edition, except where general terms of ordinary dictionary significance are used.

Botanical classification: *Hibiscus* hybrid cultivar Peppermint Schnapps.

Parentage:

*Female, or seed, parent.*—Unnamed sport of the *Hibiscus* hybrid cultivar Disco Belle Pink, not patented.

*Male or pollen parent.*—Unnamed selection of *Hibiscus coccineus,* not patented.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick becoming fibrous and enlarged; white in color.

*Rooting habit.*—Freely branching.

Plant description:

*Plant form and growth habit.*—Upright and outwardly spreading plant habit. Vigorous growth habit.

*Branching habit.*—Freely branching, usually about four lateral branches develop after pinching.

*Plant height.*—About 40 cm.

*Plant diameter* (*area of spread*).—About 43 cm.

Lateral branch description

*Length.*—About 32 cm.

*Diameter.*—About 1.4 cm.

*Internode length.*—About 1.8 cm.

*Strength.*—Strong.

*Texture.*—Smooth, glabrous.

*Color.*–146B.

Foliage description:

*Arrangement.*—Alternate, single.

*Length.*—About 14.5 cm.

*Width.*—About 12.6 cm.

*Shape.*—Palmately lobed, mapleleaf-shaped.

*Apex.*—Acuminate; reflexing.

*Base.*—Cordate.

*Margin.*—Irregularly crenate.

*Texture, upper and lower surfaces.*—Smooth, glabrous.

*Venation pattern.*—Palmate.

*Color.*—Developing and fully expanded foliage, upper surface: 147A; venation, 147B. Developing and fully expanded foliage, lower surface: 147B; venation, 147B.

*Petiole.*—Length: About 7.7 cm. Diameter: About 5 mm. Texture, upper and lower surfaces: Smooth, glabrous. Color, upper and lower surfaces: 144A.

Flower description:

*Flower arrangement.*—Flowers arranged singly originating from leaf axils. Lateral stems with typically one open flower and about nine to ten flower buds. Flowers face mostly outwardly.

*Flower appearance.*—Large, rounded pink-colored flowers with red purple-colored centers and venation. Flowers last for about four days. Flowers persistent. Flowers not fragrant.

*Natural flowering season.*—Usually spring and summer or during periods of warm weather. Early flowering habit, plants begin flowering about nine weeks after pinching.

*Flower diameter.*—About 15 cm.

*Flower length* (*height*).—About 6.5 cm.

*Flower bud.*—Length: About 5.8 cm. Diameter: About 4 cm. Shape: Ovate. Color: 65A.

*Petals.*—Arrangement: Corolla consists of five petals that are fused at base; petals imbricate. Length: About 8 cm. Width: About 9.2 cm. Shape: Obovate to fan-shaped. Apex: Rounded. Base: Acute. Margin: Entire; slightly sinuate. Texture: Upper surface: Smooth, glabrous; slightly ridge. Lower surface: Smooth, glabrous; veins prominent. Color: When opening, upper surface: 64C; venation, 63A. When opening, lower surface: More grey than 63D. Fully opened, upper surface: 65B to 65C; towards the base, 57A; venation, 63B. Color becomes closer to 65C to 65D with development. Fully opened, lower surface: 65D; venation, 53B.

*Sepals.*—Appearance: Five sepals fused at the base into a star-shaped calyx. Length: About 3.6 cm. Width: About 2.5 cm. Shape: Elliptic to ovate. Apex: Acuminate. Margin: Entire. Texture, upper surface: Smooth, glabrous. Texture, lower surface: Smooth, glabrous; ridged veins. Color, upper surface: Close to 144A to 144B. Color, lower surface: Close to 144A.

*Bracts.*—Appearance: About ten fused at base. Length: About 2.5 cm. Width: About 4 mm. Shape: Lanceolate. Apex; Acute. Margin: Entire; curved upwards. Texture, upper and lower surfaces: Smooth, glabrous. Color, upper and lower surfaces: Close to 146A to 146B.

*Peduncles.*—Length: About 4.4 cm. Diameter: About 3.5 mm. Angle: About 45° from vertical. Strength: Strong. Texture: Smooth, glabrous. Color: 146A.

*Reproductive organs.*—Androecium: Stamen number: Numerous, about 100. Filament length: About 2.5 mm. Filament color: Close to 65C. Anther shape: Round. Anther length: About 1.5 mm. Anther color: Close to 31C. Amount of pollen: Scarce. Pollen color: Close to 13B. Gynoecium: Pistil length: About 6.2 cm. Style length: About 5.3 cm. Style color: 65C to 65D. Stigma appearance: Flat; five-lobed. Stigma color: 36A. Ovary color: Close to 145C.

*Seed/fruit.*—Seed and fruit production has not been observed.

Low temperature tolerance: Plants of the new Hardy *Hibiscus* have been observed be hardy to USDA Zone 5.

Pathogen/pest resistance: Plants of the new Hardy *Hibiscus* have not been observed to be resistant to pathogens and pests common to Hardy *Hibiscus*.

It is claimed:

1. A new and distinct *Hibiscus* plant named 'Peppermint Schnapps' as illustrated and described.

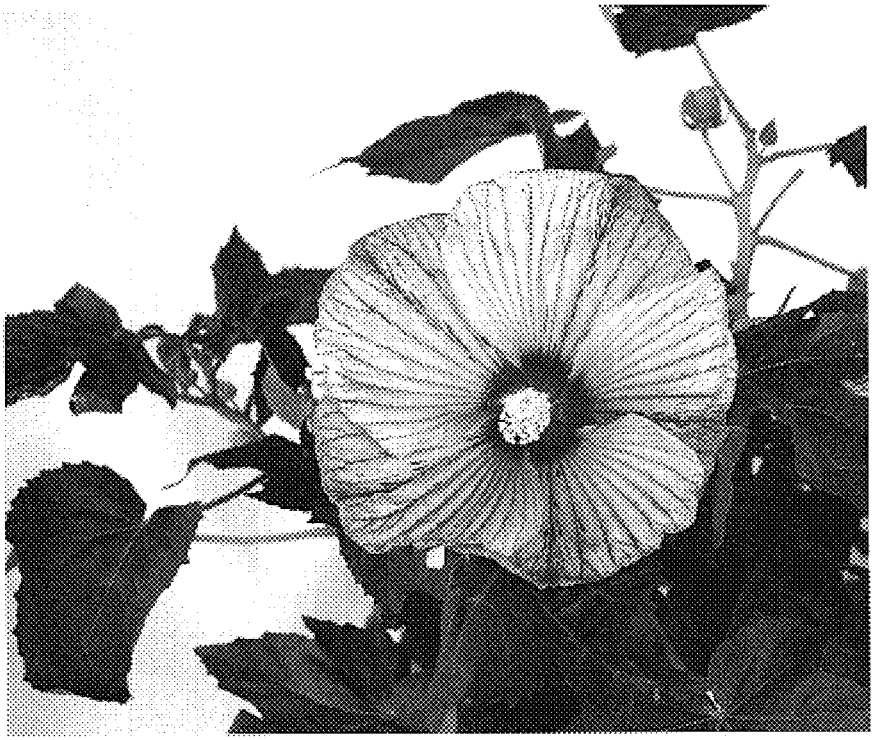
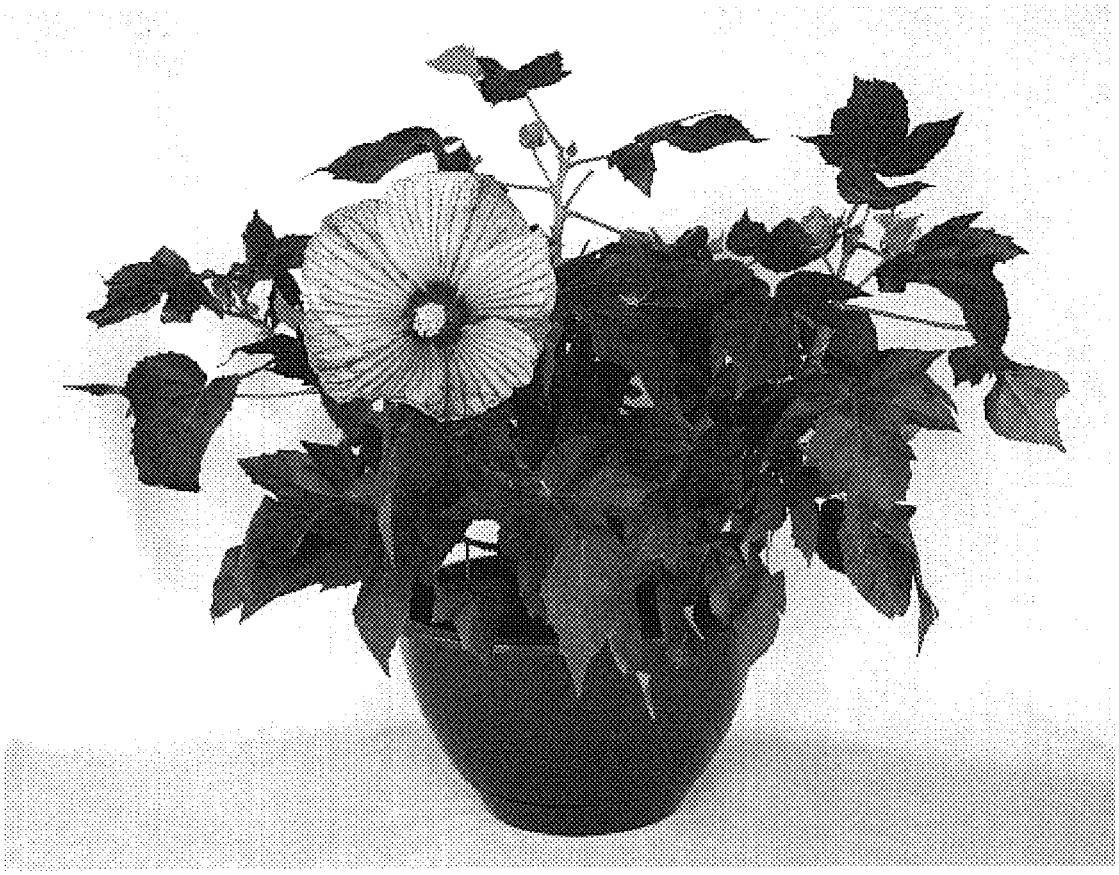

* * * * *